United States Patent [19]

Gumprecht

[11] 4,311,863
[45] Jan. 19, 1982

[54] PROCESS FOR THE MANUFACTURE OF 1,1,1,2-TETRAFLUOROETHANE

[75] Inventor: William H. Gumprecht, Wilmington, Del.

[73] Assignee: E. I. Du Pont de Nemours & Company, Wilmington, Del.

[21] Appl. No.: 158,464

[22] Filed: Jun. 11, 1980

[51] Int. Cl.$^3$ ............................................. C07C 17/20
[52] U.S. Cl. ................................................... 570/170
[58] Field of Search ................ 570/170, 162, 123, 163

[56] References Cited

U.S. PATENT DOCUMENTS 3,644,545  2/1972  Buchanan ......................... 260/653.7
4,129,603  12/1978  Bell ..................................... 260/653
4,132,741  1/1979  Besozzi ............................... 570/229

FOREIGN PATENT DOCUMENTS 697404  11/1964  Canada ................................. 570/228

OTHER PUBLICATIONS

Hudlicky, Chem. Org. Fluorine Compounds, p. 104 (1961).

Primary Examiner—Delbert E. Gantz
Assistant Examiner—Joseph A. Boska
Attorney, Agent, or Firm—F. J. Crowley

[57] ABSTRACT

2-Chloro- and 2-bromo-1,1,1-trifluoroethane react with potassium, cesium or rubidium fluoride in aqueous solution at elevated temperature under autogenous pressure to produce 1,1,1,2-tetrafluoroethane.

8 Claims, No Drawings

PROCESS FOR THE MANUFACTURE OF 1,1,1,2-TETRAFLUOROETHANE

BACKGROUND OF THE INVENTION

This invention relates to a process for the preparation of 1,1,1,2-tetrafluoroethane, also known as fluorocarbon 134a.

DESCRIPTION OF THE PRIOR ART 1,1,1,2-Tetrafluoroethane is a known compound which is useful as a refrigerant and as an aerosol propellant. U.S. Pat. No. 2,885,427 issued May 5, 1959, discloses the preparation of this fluorocarbon by the reaction of trichloroethylene with hydrogen fluoride in the presence of a catalyst prepared by heating hydrated chromium fluoride in the presence of oxygen. The resultant product is a mixture of fluorocarbons in which 1,1,1,2-tetrafluoroethane is reported as being present in an amount of 3 mol %. In a more recent patent, U.S. Pat. No. 4,129,603 issued Dec. 12, 1978, 1,1,1-trifluoro-2-chloroethane is reacted with hydrogen fluoride in the presence of a chromium oxide catalyst to produce a fluorocarbon mixture in which the 1,1,1,2-tetrafluoroethane content is reported as 18.2% by volume.

It is apparent from the prior art that the chlorine atom of the —$CH_2Cl$ group is highly resistant to halogen exchange with HF. Hudlicky in Chemistry of Organic Fluorine Compounds, MacMillan Co., New York, NY (1962), p. 93 and Buckman in U.S. Pat. No. 3,644,545 speak of the difficulty of fluorine exchange on —$CH_2Cl$ groups by antimony catalyzed liquid phase reaction and vapor phase reaction respectively.

SUMMARY OF THE INVENTION

According to the present invention, 1,1,1,2-tetrafluoroethane is produced by intimately contacting, at a temperature of about 200° to 300° C. under autogenous pressure, 2-chloro-1,1,1-trifluoroethane with about one to five molar proportions of an alkali metal fluoride selected from the group consisting of potassium, cesium, and rubidium fluoride in 25 to 65 weight % aqueous solution. In a more preferred embodiment of this process, the reaction mixture may contain up to 1 mole of hydrogen fluoride per mole of alkali metal fluoride used. In a further embodiment of the invention, a surface active agent is added in a minor amount sufficient to promote contact between the liquid-gas phases in the reaction, thus increasing the yield of 1,1,1,2-tetrafluoroethane. 2-Bromo-1,1,1-trifluoroethane reacts analogously, optimally at about 250° C.

DETAILED DESCRIPTION

The present invention involves intimately contacting 2-chloro- or 2-bromo-1,1,1-trifluoroethane in the gaseous state with an aqueous solution of an alkali metal fluoride to produce 1,1,1,2-tetrafluoroethane. Intimate contact between the gaseous and the liquid phase can be accomplished by agitation, such as by stirring, shaking or bubbling the gaseous reactant into the liquid phase. In the reaction that takes place, the chlorine atom of the —$CH_2Cl$ group of 2-chloro-1,1,1-trifluoroethane is replaced with fluorine. When 2-bromo-1,1,1-trifluoroethane is used, a similar reaction takes place replacing the bromine atom with fluorine. The reaction is initiated by heating an agitated mixture of the halo-1,1,1-trifluoroethane and an aqueous solution of KF, CsF or RbF or mixtures of these fluorides under autogenous pressure conditions. When using KF, the minimum temperature at which substantial yields are obtained in 30 to 60 hours is about 200° C. It is preferred, however, to carry out the reaction at about 300° C. where relatively high yields are obtained in one or two hours. The concentration of the alkali metal fluoride should be between about 25 wt % and about 60 wt % of the aqueous solution. It is preferred to employ KF in an amount of about 40 wt %. The mole ratio of alkali metal fluoride to the 2-bromo- or 2-chloro-1,1,1-trifluoroethane may be between about 1 and about 5 with the preferred ratio being about 3 to 4.5. It is also preferred to have HF present during the reaction although it is not an essential reactant. The amount of HF can range up to 1 mole per mole of alkali metal fluoride while an amount of about 0.33 mole per mole of alkali metal fluoride is preferred. It is believed that the HF combines with the alkali metal fluoride to form a bifluoride. When the HF is added as an aqueous solution, the amount of water present in the HF should be taken into account in adjusting concentrations of the reaction solution to within the ranges specified herein.

Surface active agents are useful in improving yield, probably as a result of improving contact between phases. The nature of the surface active agent is not critical so long as the activity is not impaired by the basic to slightly acid reaction medium. The amount of surface active agent can range from about 0.5–15% by weight of the aqueous solution. A preferred surfactant is the lithium salt of a perfluorosulfonic acid of the formula $C_{6-8}F_{13-17}SO_3Li$. The reaction proceeds best in acid solution as can be demonstrated by adding alkaline potassium borate buffer which inhibits the reaction whereas the addition of HF improves the yield. It is preferred to employ an amount of HF not in excess of the number of moles of alkali fluoride. It has been found that 2,2,2-trifluoroethanol can be a by-product of the reaction. This by-product apparently comes about from a competing hydrolysis reaction. Its formation may be suppressed by the addition of HF.

The reaction mixtures of the invention are corrosive to some materials of construction such as stainless steel. High copper content alloys, molybdenum and the noble metals are suggested as materials of construction for the reaction.

EXAMPLES

Experimental Procedure

Reactions were carried out in a 400 ml Hastelloy shaker tube. The open shaker tube was flushed with nitrogen and, under nitrogen blanket, all reactants, except 2-chloro-1,1,1-trifluoroethane, were charged to the tube. When HF was used, it was charged in the form of 49% commercial aqueous HF. The closed shaker tube was chilled in a solid $CO_2$/methanol bath and evacuated. 2-Chloro-1,1,1-trifluoroethane was charged to the tube by distillation from a tared cylinder on a balance.

The closed tube was mounted in a heater-shaker device and heated. On reaching temperature, shaking was begun. In the absence of shaking, essentially no reaction took place.

In some experiments the pressure was measured by means of a pressure gauge attached to the tube. Observed pressures were typically 1500 to 2500 psig (104–173 Pa abs.).

At the end of the reaction time the warm tube at about 90°–95° C. was connected to a simple recovery train comprising in series an ice-cooled trap, to collect the bulk of codistilled water, a $CaSO_4$ dryer, and a tared, open-ended, stainless steel collector cylinder equipped with a dip tube, and chilled with a solid $CO_2$/methanol mixture. Small bubblers before and after the cylinder allowed flow rate control. If unreacted 2-chloro-1,1,1-trifluoroethane was seen to collect in the ice-cooled trap, it was warmed at the end of the products recovery to distill the ethane into the collector cylinder.

A sample of the liquid phase in the chilled collector cylinder was analyzed by gas chromatography. Results are reported in the following tables in response-corrected weight percent. Table I shows the results of 36 trials in which HF was not charged. Table II shows similar results of 15 trials in which HF was charged to the reactor mixture. Table III shows the results of three trials using 2-bromo-1,1,1-trifluoroethane as organic starting material and two comparative trials using 2-chloro-1,1,1-trifluoroethane as starting material.

TABLE II

RESULTS FOR ONE HOUR REACTION WITH 0.5 MOLE OF $CF_3CH_2Cl$ AT $300 \pm 6°$ C. IN THE PRESENCE OF HF

| Ex. No. | KF Conc. (Wt %) (1) | MOLAR $F^-/$ $CF_3CH_2Cl$ | S.A.A. (Wt %) (1) (2) | HF (Wt %) (1) | Conv. (%) | Yield (%) |
|---|---|---|---|---|---|---|
| 37 | 40 | 3.0 | 0.7 | 13.8 | 37.6 | 93.0 |
| 38 | 41 | 4.5 | 0.7 | 11.0 | 87.1 | 86.9 |
| 39 | 41 | 4.5 | 0.7 | 12.5 | 75.5 | 86.7 |
| 40 | 41 | 4.5 | 0.7 | 9.4 | 92.1 | 84.1 |
| 41 | 40 | 4.5 | 0.7 | 4.6(3) | 97.7 | 83.7 |
| 42 | 40 | 3.0 | 0.7 | 4.6 | 90.0 | 83.5 |
| 43 | 41 | 4.5 | 0.7 | 7.8 | 94.5 | 82.8 |
| 44 | 40 | 4.5 | 0.7 | 4.6(3) | 98.2 | 81.9 |
| 45 | 41 | 4.5 | 0.7 | 6.3 | 97.9 | 81.7 |
| 46 | 30 | 4.0 | 0.7 | 10.3 | 90.1 | 81.5 |
| 47 | 30 | 4.0 | 0.7 | 10.3 | 88.5 | 81.0 |
| 48 | 40 | 4.5 | 0.7 | 4.6(3) | 98.9 | 76.1 |
| 49 | 41 | 4.5 | 0.7 | 14.1 | 75.8 | 84.6 |
| 50 | 30 | 4.0 | 0.7 | 10.3 | 83.6* | 68.9* |
| 51 | 41 | 4.5 | 0.7 | 12.5 | 79.7 | 63.2* |
| Comparison | | | | | | |
| A | 73(4) | 3.0 | 1.3 | 25.3 | 0.0 | 0.0 |

TABLE 1

RESULTS USING ALKALI METAL FLUORIDE WITH NO HF PRESENT

| Ex. No. | Temp. (°C.) ±5 | Time (Hr) | Moles $CF_3CH_2Cl$ | KF Conc. (wt %) (1) | Molar $F^-/$ $CF_3CH_2Cl$ | Additional Components (wt %) (1) | Conv. (%) | Yield (%) |
|---|---|---|---|---|---|---|---|---|
| 1 | 300 | 2 | 0.75 | 40.1 | 2 | (4) | 91.3 | 68.8 |
| 2 | 300 | 2 | 0.75 | 40.1 | 2 | (4) | 88.7 | 69.1 |
| 3 | 300 | 2 | 0.75 | 40.1 | 2 | (4) | 86.5 | 65.3 |
| 4 | 250 | 36 | 0.75 | 61.7 | 2 | — | 92.2 | 83.0 |
| 5 | 250 | 36 | 0.75 | 49.2 | 2 | — | 77.7 | 76.3 |
| 6 | 300 | 4 | 0.75 | 49.2 | 2 | — | 85.0 | 72.5 |
| 7 | 300 | 2 | 0.75 | 42.3 | 2 | — | 97.5 | 73.7 |
| 8 | 300 | 1 | 0.75 | 40.1 | 2 | (2) 0.7(3) | 81.1 | 72.0 |
| 9 | 300 | 1 | 0.75 | 40.1 | 2 | 0.7(3) | 86.3 | 71.2 |
| 10 | 300 | 2 | 0.75 | 40.1 | 2 | (4) | 87.0 | 71.2 |
| 11 | 300 | 2 | 0.75 | 49.2 | 2 | — | 74.8 | 70.9 |
| 12 | 300 | 1 | 0.50 | 39.8 | 3 | 0.7(3) | 93.3 | 70.2 |
| 13 | 300 | 2 | 0.50 | 40.1 | 3 | (4) | 94.6 | 70.2 |
| 14 | 300 | 2 | 0.75 | 61.7 | 2 | (2) | ~34 | ~69 |
| 15 | 300 | 6 | 0.75 | 61.7 | 2 | (2) | 76.0 | 68.9 |
| 16 | 300 | 2 | 0.75 | 49.2 | 2 | — | 79.6 | 68.5 |
| 17 | 300 | 6 | 0.75 | 61.7 | 2 | (2) | ~83 | ~68 |
| 18 | 250 | 36 | 0.75 | 34.5(6) | 2 | 1.1(5) | 88.6 | 66.8 |
| 19 | 250 | 36 | 0.75 | 36.4 | 2 | 1.1(5) | 90.5 | 65.9 |
| 20 | 300 | 6 | 0.50 | 40.1 | 3 | (4) | 96.9 | 65.3 |
| 21 | 200 | 60 | 0.75 | 59.7(8) | 2 | 1.0(7) | 48.9 | 65.1 |
| 22 | 300 | 6 | 0.75 | 49.2 | 2 | — | 92.1 | 64.8 |
| 23a | 145 | 36 | 0.75 | 33.2 | 2 | 9.7(5) | 8.5 | 11.7 |
| 23b | 200 | 36 | 0.75 | ~33.2(10) | 2 | ~9.7(5)(10) | 57.1 | 64.2 |
| 24 | 320 | ¼ | 0.50 | 40.1 | 3 | 0.7(3) | 87.2 | 64.0 |
| 25 | 300 | 1 | 0.75 | 40.1 | 2 | (2) | 74.1 | 68.9 |
| 26 | 250 | 16 | 0.75 | 61.3 | 2 | 1.4(3) | 41.5 | 63.1 |
| 27 | 200 | 60 | 0.75 | 36.4 | 2 | 1.1(5) | 33.2 | 59.9 |
| 28 | 325 | 4 | 0.75 | 61.7 | 2 | — | 78.8 | 59.3 |
| 29 | 200 | 36 | 0.75 | 32.6 | 2 | 11.2(7) | 62.2 | 58.9 |
| 30 | 300 | 2 | 0.75 | 54.8 | 2 | (2) | 60.7 | 58.7 |
| 31 | 250 | 16 | 0.75 | 61.7 | 2 | — | 40.5 | 57.7 |
| 32 | 250 | 36 | 0.75 | 33.2 | 2 | 9.5(5) | 90.1 | 50.6 |
| 33 | 300 | 2 | 0.75 | 61.7 | 2 | (2) | 19.9 | 49.8 |
| 34 | 200 | 60 | 0.75 | 36.2 | 2 | 1.6(7) | 33.8 | 47.3 |
| 35 | 200 | 60 | 0.75 | 37.4(9) | 2 | 1.6(7) | 46.0 | 47.3 |
| 36 | 200 | 60 | 0.75 | 34.3(6) | 2 | 1.6(7) | 32.8 | 43.5 |

Footnotes:
(1) Wt % on basis of the reaction mixture, excluding 2-chloro-1,1,1-trifluoroethane.
(2) "Hastelloy" B, C, "Inconel" 600, Carpenter Alloy 20, 316 stainless steel test coupons present.
(3) $C_{6-8}F_{13-17}SO_3Li$.
(4) "Monel", "Hastelloy" B, C, "Inconel" 625 test coupons present.
(5) Tetra-n-butyl phosphonium bromide.
(6) and 1.9 wt % CsF.
(7) Tri-n-butyl hexadecyl phosphonium bromide.
(8) Wt % of CsF alone
(9) In 150 ml water/diethylene glycol 1:1 (vol).
(10) The aqueous heel from Example 23a was reused with fresh 2-chloro-1,1,1-trifluoroethane.

TABLE II-continued
RESULTS FOR ONE HOUR REACTION WITH 0.5 MOLE OF CF$_3$CH$_2$Cl AT 300 ± 6° C. IN THE PRESENCE OF HF

| Ex. No. | KF Conc. (Wt %) (1) | MOLAR F$^-$/ CF$_3$CH$_2$Cl | S.A.A. (Wt %) (1) (2) | HF (Wt %) (1) | Conv. (%) | Yield (%) |
|---|---|---|---|---|---|---|
| B | 36 | 4.5 | 0.7 | 15.1(5) | 47.3 | 72.7 |

*Data considered to be uncertain.
Footnotes:
(1) On the basis of the reaction mixture, excluding CF$_3$CH$_2$Cl
(2) S.A.A. = surface active agent (C$_{6-8}$F$_{13-17}$SO$_3$Li)
(3) "Monel", Ni, Cu/Ni (70/30), No test coupons present
(4) KF . HF fused, no water
(5) 10.2 wt % KCl added

TABLE III
RESULTS USING 2-BROMO-1,1,1-TRIFLUOROETHANE TOGETHER WITH COMPARATIVE RUNS USING 2-CHLORO-1,1,1-TRIFLUOROETHANE

| Ex. No. | Temp. (°C.) ±5 | Time (Hr) | Moles CF$_3$CH$_2$X | KF Conc. (wt %) (1) | HF (wt %) (1) | Molar F$^-$/ CF$_3$CH$_2$X | X | Conv. (%) | Yield (%) |
|---|---|---|---|---|---|---|---|---|---|
| 52 | 300 | 1 | 0.50 | 40 | 4.6 | 4.5 | Cl | 98 | 84 |
| 53 | 300 | 1 | 0.51 | 40 | 4.6 | 4.4 | Br | 99 | 87 |
| 54 | 300 | 1 | 0.53 | 40 | 0 | 2.8 | Br | 96 | 75 |
| 55 | 250 | 2 | 0.42 | 40 | 4.6 | 5.4 | Br | 88 | 90 |
| 56 | 250 | 2 | 0.44 | 40 | 4.6 | 5.1 | Cl | 79 | 31 |

All of the mixtures in Table III contained 0.7 wt % C$_{6-8}$F$_{13-17}$SO$_3$Li based on the weight of the reaction mixture excluding CF$_3$CH$_2$X
(1) Wt. % on basis of reaction mixture excluding CF$_3$CH$_2$X Examination of the tables suggests that, in the absence of HF, as in Table I, temperatures of 300° C. are needed to obtain yields over 80% in two hours whereas, under similar conditions, in the presence of HF, yields of 80% and more are obtained in one hour. However, HF in the absence of water does not further the reaction as is demonstrated by Comparison A of Table II wherein 2-chloro-1,1,1-trifluoroethane was contacted with fused KF.HF with no water present. No reaction occurred.

The aqueous reaction medium used in the invention does not appear to be sensitive to chloride ion concentration as demonstrated by Comparison B where it is seen that the reaction is not strongly inhibited by the addition of substantial amounts of potassium chloride to the reaction mixture.

Table III demonstrates that 2-bromo-1,1,1-trifluoroethane reacts with potassium fluoride in satisfactory yields at 250° C. in one to two hours under conditions which require 300° C. for satisfactory yields when the chloride analogue is employed as starting material.

I claim:

1. A process for the preparation of 1,1,1,2-tetrafluoroethane comprising intimately contacting, at a temperature of about 200° C. to 300° C. under autogenous pressure, a 2-halo-1,1,1-trifluoroethane selected from the group consisting of 2-chloro-1,1,1-trifluoroethane and 2-bromo-1,1,1-trifluoroethane with about one to five molar proportions of an alkali metal fluoride selected from the group consisting of potassium, cesium and rubidium fluoride in 25 to 65 weight % aqueous solution.

2. The process of claim 1 in which the 2-halo-1,1,1-trifluoroethane is 2-chloro-1,1,1-trifluoroethane.

3. The process of claim 2 in which the alkali metal fluoride is potassium.

4. The process of claim 3 in which hydrogen fluoride is present in an amount up to 1 mole per mole of alkali metal fluoride.

5. The process of claim 3 in which hydrogen fluoride is present in an amount of about 0.33 mole per mole of alkali metal fluoride.

6. The process of claim 3 in which a surface active agent is present in an amount of 0.5-15% by weight of the aqueous solution.

7. The process of claim 4 in which a surface active agent is present in an amount of 0.5-15% by weight of the aqueous solution.

8. The process of claim 7 in which the surface active agent is C$_{6-8}$F$_{13-17}$SO$_3$Li.

* * * * *